(12) United States Patent
Abdel-Magid et al.

(10) Patent No.: US 7,582,753 B2
(45) Date of Patent: Sep. 1, 2009

(54) PROCESS FOR THE PREPARATION OF BENZOTRIAZEPINE DERIVATIVES

(75) Inventors: Ahmed F. Abdel-Magid, Ambler, PA (US); Luigi Anzalone, West Chester, PA (US); Judith Cohen, North Wales, PA (US); Steven Mehrman, Quakertown, PA (US); Frank Villani, Perkasie, PA (US)

(73) Assignee: JanssenPharmaceutica, NV, Beerse (BE)

( * ) Notice: Subject to any disclaimer, the term of this patent is extended or adjusted under 35 U.S.C. 154(b) by 212 days.

(21) Appl. No.: 11/531,794

(22) Filed: Sep. 14, 2006

(65) Prior Publication Data

US 2007/0066819 A1    Mar. 22, 2007

Related U.S. Application Data

(60) Provisional application No. 60/717,658, filed on Sep. 16, 2005.

(51) Int. Cl.
*C07D 255/04*   (2006.01)
(52) U.S. Cl. .................................................. 540/501
(58) Field of Classification Search ................. 540/501; 514/183
See application file for complete search history.

(56) References Cited

FOREIGN PATENT DOCUMENTS

WO    WO 03/041714 A1    5/2003
WO    WO 2004/098609    11/2004
WO    WO 2006/129120    12/2006

OTHER PUBLICATIONS

Morgenstern, O., et al., "Studies on the Synthesis of 5-Benzyl-1,3,4-Benzotriazepinen from 2-Isothiocyanatodesoxybenzoin", Pharmazie, Die, Govi Verlag, Eschborn, DE, vol. 47, No. 1, 1992, pp. 25-28.

Shevchenko, V.V. et al., Abstract, Journal of Organic Chemistry, USSR, vol. 11, 1975, pp. 1189-1191 & Beilstein Institute for Organic Chemistry, Frankfurt-Main, DE; XP002419945, Database Accession No. 1413209.

"Efficient Synthesis of a-Chloro Ketones via Reaction of Organometallic Reagents with N-Methoxy-N-Methychloroacetamide". R. Tillyer, L.F. Frey, D.M. Tschaen and U,-H. Dolling. Department of Process Research, Merck Research Laboratories, Rahway NJ, USA 07065. Mar. 1996, SYNLETT. p. 225-226.

"Chemie und biologische Aktivitat von 1, 3, 4-Benzotriazephinen". P. Richter und O. Morgenstern. Die Pharmazie 39 (1984), H.5 301-314.

PCT Partial International Search Report, dated Mar. 9, 2007, for PCT Int'l. Appln. No. PCT/US2006/035887.

*Primary Examiner*—Bruck Kifle
(74) *Attorney, Agent, or Firm*—Mary A. Appollina

(57) ABSTRACT

The present invention is directed to a novel process for the preparation of benzo[e][1,2,4]triazepin-2-one derivatives, useful in the preparation of gastrin and cholecystokinin receptor ligands.

3 Claims, No Drawings

PROCESS FOR THE PREPARATION OF BENZOTRIAZEPINE DERIVATIVES

CROSS REFERENCE TO RELATED APPLICATIONS

This application claims the benefit of U.S. Provisional Application 60/717,658, filed on Sep. 16, 2005, which is incorporated by reference herein in its entirety.

FIELD OF THE INVENTION

The present invention is directed to novel processes for the preparation of benzotriazepine derivatives which are useful as gastrin and cholecystokinin receptor ligands.

BACKGROUND OF THE INVENTION

PCT publication WO 2003/041714, which is herein incorporated by reference, discloses benzotriazepine derivatives useful as gastrin and cholecystokinin receptor ligands. PCT publication WO 2003/041714 further discloses a process for the preparation of the benzotriazepine derivatives. This process however involves a slow reaction step and requires the use of excess ethyl hydrazine acetate (an expensive reagent), which makes the disclosed process disadvantageous for large scale/commercial production.

The process of the present invention is advantageous over the prior art process by using smaller amounts of ethyl hydrazine acetate reactant and/or requiring shorter reaction times.

SUMMARY OF THE INVENTION

The present invention is directed to a process for the preparation of compounds of formula (I)

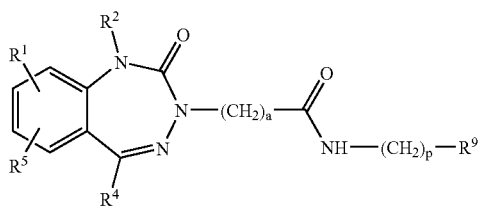

(I)

wherein $R^1$ and $R^5$ are independently H, $C_1$ to $C_6$ alkyl, ($C_1$ to $C_6$ alkyl)oxy, thio, ($C_1$ to $C_6$ alkyl)thio, carboxy, carboxy($C_1$ to $C_6$ alkyl), formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, hydroxy($C_1$ to $C_6$ alkyl), amino, ($C_1$ to $C_6$ alkyl)amino, di($C_1$ to $C_6$ alkyl)amino, aminocarbonyl, halo, halo($C_1$ to $C_6$ alkyl)sulfonylamino, ($C_1$ to $C_6$ alkyl)aminocarbonyl, di($C_1$ to $C_6$ alkyl)aminocarbonyl, [N-Z]($C_1$ to $C_6$ alkyl)carbonylamino, formyloxy, formamido, ($C_1$ to $C_6$ alkyl)aminosulfonyl, di($C_1$ to $C_6$ alkyl)aminosulfonyl or [N-Z]($C_1$ to $C_6$ alkyl)sulfonylamino;

or $R^1$ and $R^5$ together form a methylenedioxy group; provided that $R^1$ and $R^5$ are bound at adjacent carbon atoms;

Z is H, $C_1$ to $C_6$ alkyl, t-butoxycarbonyl, acetyl, benzoyl or benzyl;

$R^2$ is H or an optionally substituted C1 to C18 hydrocarbyl group wherein up to three C atoms may optionally be replaced by N, O and/or S atoms;

alternatively, $R^2$ is —$(CH_2)_s$—C(O)—$(CH_2)_t$—$R^8$ wherein s is 0, 1, 2 or 3;

t is 0, 1, 2 or 3;

$R^8$ is selected from H, OH, $C_1$ to $C_{12}$ alkyl, ($C_1$ to $C_{12}$ alkyl)oxy, $C_3$ to $C_{12}$ cycloalkyl, phenyl, naphthyl, pyridyl, pyrrlyl, imidazolyl, pyrazolyl, pyridazinyl, pyrimidinyl, triazolyl, furanyl, thienyl, furazanyl, oxazoylyl, isoxazolyl, thiazolyl, thiazinyl, indolyl, indolinyl, idoindolyl, isoindolinyl, isoquinolinyl, quinolinyl, benzofuranyl, benzothienyl, piperazinyl, piperidinyl, pyrrolidinyl, pyrrolinyl, dihydropyranyl, tetrahydropyranyl, pyranyl, tetrahydrofuranyl, morpholinyl, thiazolidinyl, thiomorpholinyl or thioxanyl;

(all optionally substituted with 1, 2 or 3 groups independently selected from $C_1$ to $C_6$ alkyl, ($C_1$ to $C_6$ alkyl)oxy, thio, ($C_1$ to $C_6$ alkyl)thio, carboxy, carboxy($C_1$ to $C_6$ alkyl), formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, hydroxy($C_1$ to $C_6$ alkyl), amino, ($C_1$ to $C_6$ alkyl)amino, di($C_1$ to $C_6$ alkyl)amino, aminocarbonyl, halo, halo($C_1$ to $C_6$ alkyl) aminosulfonyl or ($C_1$ to $C_6$ alkyl)sulfonylamino);

$R^4$ is an optionally substituted $C_1$ to $C_{18}$ hydrocarbyl group wherein up to three C atoms may be optionally be replaced by N, O and /or S atoms;

alternatively, $R^4$ is —$(CH_2)_q$-T-$R^{10}$;

wherein q is 0, 1, 2, or 3;

T is a bond, O, S, NH or N($C_1$ to $C_6$ alkyl); provided that when T is O, S, NH or N($C_1$ to $C_6$ alkyl) then q is 1, 2 or 3;

$R^{10}$ is $C_1$ to $C_{12}$ alkyl, $C_3$ to $C_{12}$ cycloalkyl, phenyl, naphthyl, pyridyl, pyrrolyl, imidazolyl, pyrazolyl, pyrizadinyl, pyrimidinyl, triazolyl, furanyl, thienyl, furazanyl, oxazolyl, isoxazolyl, thiazolyl, thiazinyl, indolyl, indolinyl, isoindolinyl, isoquinolinyl, quinolinyl, benzofuranyl, benzothienyl, piperazinyl, piperidinyl, pyrrolidinyl, pyrrolinyl, dihydropyranyl, tetrahydropyranyl, pyranyl, tetrahydrofuranyl, morpholinyl, thiazolidinyl, thiomorpholinyl or thioxazyl;

(all optionally substituted with 1, 2 or 3 groups independently selected from $C_1$ to $C_6$ alkyl, ($C_1$ to $C_6$ alkyl)oxy, $C_3$ to $C_8$ cycloalkyl, ($C_3$ to $C_8$ cycloalkyl)oxy, thio, ($C_1$ to $C_6$ alkyl)thio, carboxy, carboxy($C_1$ to $C_6$ alkyl), formyl, ($C_1$ to $C_6$ alkyl)carbonyl, ($C_1$ to $C_6$ alkyl)oxycabronyl, ($C_1$ to $C_6$ alkyl)carbonyloxy, nitro, trihalomethyl, hydroxy, hydroxy($C_1$ to $C_6$ alkyl), amino, ($C_1$ to $C_6$ alkyl)amino, di($C_1$ to $C_6$ alkyl)amino, aminocarbonyl, halo, halo($C_1$ to $C_6$ alkyl), aminosulfonyl, ($C_1$ to $C_6$ alkyl)sulfonylamino or cyano);

with the proviso that $R^{10}$ is not phenyl or substituted phenyl when q is 0 and T is a bond;

provide that when $R^2$ is —$(CH_2)_s$—C(O)—$(CH_2)_t$—$R^8$ then $R^4$ is not —$(CH_2)_q$-T-$R^{10}$; provided further than when $R^4$ is —$(CH_2)_q$-T-$R^1$ then $R^2$ is not —$(CH_2)_s$—C(O)—$(CH_2)_t$—$R^8$;

a is 1, 2, 3 or 4;

p is 0, 1 or 2;

$R^9$ is H, $C_1$ to $C_6$ alkyl, phenyl, naphthyl, pyridyl, benzimidazolyl, indazolyl, quinolinyl, isoquinolinyl, tetrahydroisoquinolinyl, indolinyl, isoindolinyl, indolyl, isoindolyl, 2-pyridonyl;

all optionally substituted with 1, 2 or 3 groups independently selected from -L-Q;

wherein L is a bond or a group of the formula —$(CR^{17}R^{18})_v$—Y—$(CR^{17}R^{18})_w$;

wherein c and w are independently 0, 1, 2, or 3;

Y is a bond, —$CR^{15}$=$CR^{16}$, phenyl, furanyl, thiophenyl, pyrrolyl, thiazolyl, imidazolyl, oxazolyl, isoxazolyl, pyrazolyl, isoxazolonyl, piperazinyl, piperidinyl, morpholinyl, pyrrolidinyl, iosthiazolyl, triazolyl, oxadiazolyl, thiadiazolyl, pyridyl or pyridazyl;

Q is H, ($C_1$ to $C_6$ alkyl)oxy, [N-Z]($C_1$ to $C_6$ alkyl)oxy($C_1$ to $C_6$ alkyl)amino, thio, ($C_1$ to $C_6$ alkyl)thio, carboxy($C_1$ to $C_6$ alkyl)thio, carboxy, carboxy($C_1$ to $C_6$ alkyl), carboxy($C_1$ to $C_6$ alkenyl), [N-Z]carboxy($C_1$ to $C_6$ alkyl)amino, carboxy($C_1$ to $C_6$ alkyl)oxy, formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydrxy, amino, [N-Z]($C_1$ to $C_6$ alkyl)amino, aminocarbonyl, $C_1$ to $C_6$ alkyl)aminocarbonyl, di($C_1$ to $C_6$ alkyl)aminocarbonyl, [N-Z]($C_1$ to $C_6$ alkyl)carbonyl($C_1$ to $C_6$ alkyl)amino, halo, halo($C_1$ to $C_6$ alkyl), sulfamoyl, [N-Z]($C_1$ to $C_6$ alkyl)sulfonylamino, ($C_1$ to $C_6$ alkyl)sulfonylaminocarbonyl, carboxy($C_1$ to $C_6$ alkyl)sulfonyl, carboxy($C_1$ to $C_6$ alkyl)sulfinyl, tetrazolyl, [N-Z]tetrazolylamino, cyano, amidino, amidinothio, $SO_3H$, formyloxy, formamido, $C_3$ to $C_8$ cycloalkyl, ($C_1$ to $C_6$ alkyl)sulphamoyl, di($C_1$ to $C_6$ alkyl)sulphamoyl, ($C_1$ to $C_6$ alkyl)carbonylaminosulfonyl, 5-oxo-2,5-dihydro[1,2,4]oxadiazolyl, carboxy($C_1$ to $C_6$ alkyl)carbonylamino, tetrazolyl($C_1$ to $C_6$ alkyl)thio, [N-Z]tetrazolyl($C_1$ to $C_6$ alkyl)amino, 5-oxo-2,5-dihydro-[1,2,4]thiadiazolyl, 5-oxo-1,2-dihydro[1,2,4]triazolyl, [N-Z]($C_1$ to $C_6$ alkyl)amino($C_1$ to $C_6$ alkyl)amino or a group of the formula

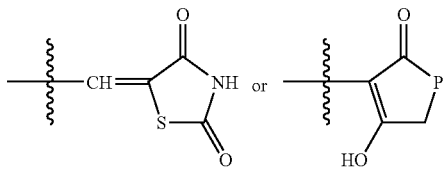

wherein P is O, S or $NR^{19}$;

$R^{11}$, $R^{12}$, $R^{13}$ and $R^{14}$, R15, $R^{17}$, $R^{18}$ and $R^{19}$ are independently H or $C_1$ to $C_3$ alkyl; and $R^{16}$ is H, $C_1$ to $C_3$ alkyl or acetylamino;

or a pharmaceutically acceptable salt thereof;

comprising

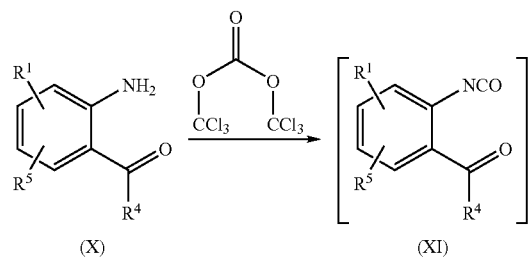

reacting a compound of formula (X), with phosgene or a phosgene equivalent; in the presence of an organic base; in an aprotic organic solvent; to yield the corresponding compound of formula (XI);

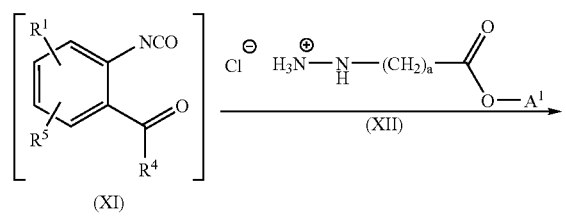

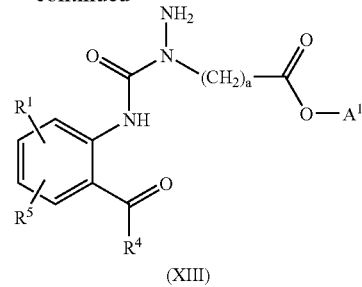

reacting the compound of formula (XI), with a compound of formula (XII), wherein $A^1$ is $C_{14}$alkyl; in the presence of an organic base; in an aprotic organic solvent; to yield the corresponding compound of formula (XIII);

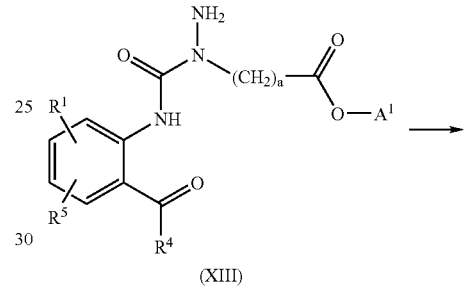

reacting the compound of formula (XIII) with an acid; in an organic solvent; to yield the corresponding compound of formula (XIV);

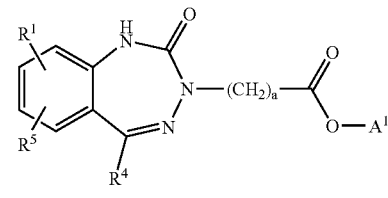

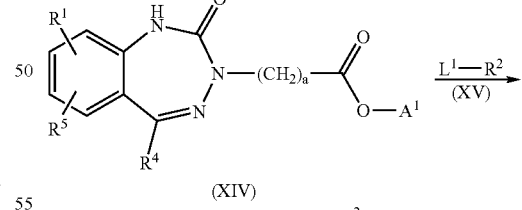

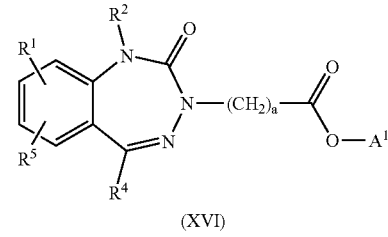

reacting the compound of formula (XIV) with a compound of formula (XV), wherein $L^1$ is a suitable leaving group; in the presence of an organic or inorganic base; in an organic solvent; provided that when the leaving group is chloro, a source of iodide is present; to yield the corresponding compound of formula (XVI);

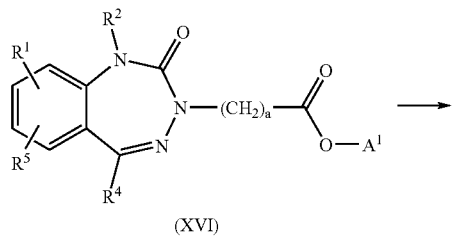

(XVI)

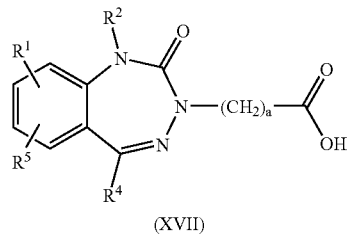

(XVII)

reacting the compound of formula (XVI) with an aqueous base to yield the corresponding compound of formula (XVII);

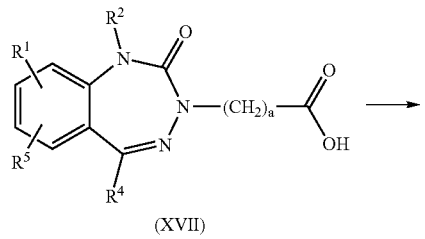

(XVII)

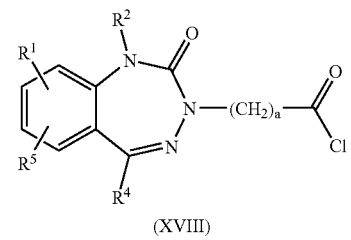

(XVIII)

reacting the compound of formula (XVII) with a chlorinating agent; in an organic solvent; to yield the corresponding compound of formula (XVIII);

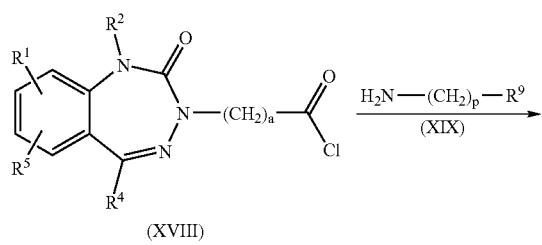

(XVIII)

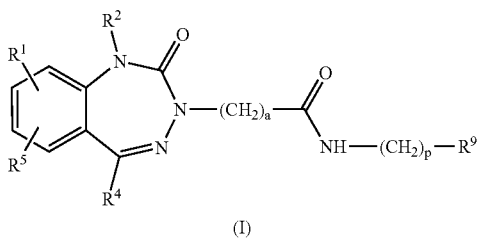

(I)

reacting the compound of formula (XVIII) with a compound of formula (XIX); in the presence of an organic base; in an aprotic organic solvent; to yield the corresponding compound of formula (I).

In an embodiment, the present invention is directed to a process for the preparation of the compound of formula (Is)

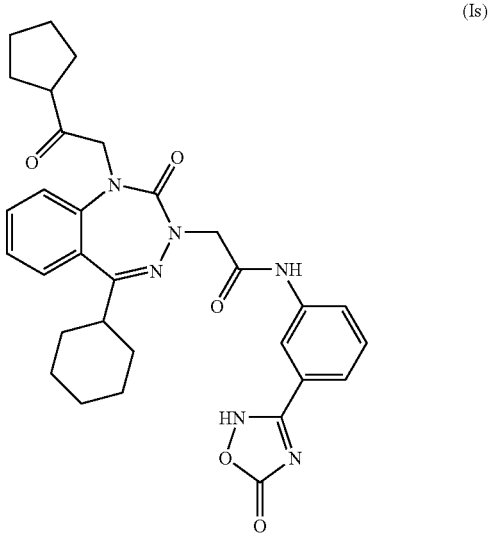

(Is)

also known as 2-[5-cyclohexyl-1-(2-cyclopentyl-2-oxo-ethyl)-2-oxo-1,2-dihydro-benzo[e][1,2,4]triazepin-3-yl]-N-[3-(5-oxo-2,5-dihydro-[1,2,4]oxadiazol-3-yl)-phenyl]-acetamide, or a pharmaceutically acceptable salt thereof;

comprising

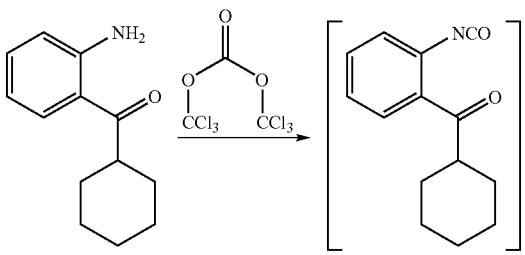

reacting (2-amino-phenyl)-cyclohexyl-methanone with phosgene or a phosgene equivalent; in the presence of an organic base; in an aprotic organic solvent; to yield cyclohexyl-(2-isocyanato-phenyl)-methanone;

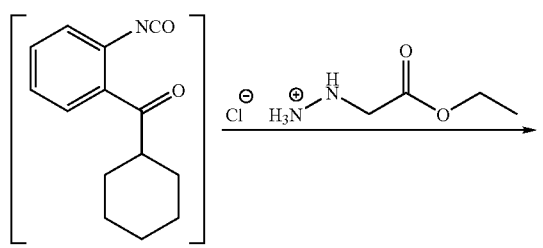

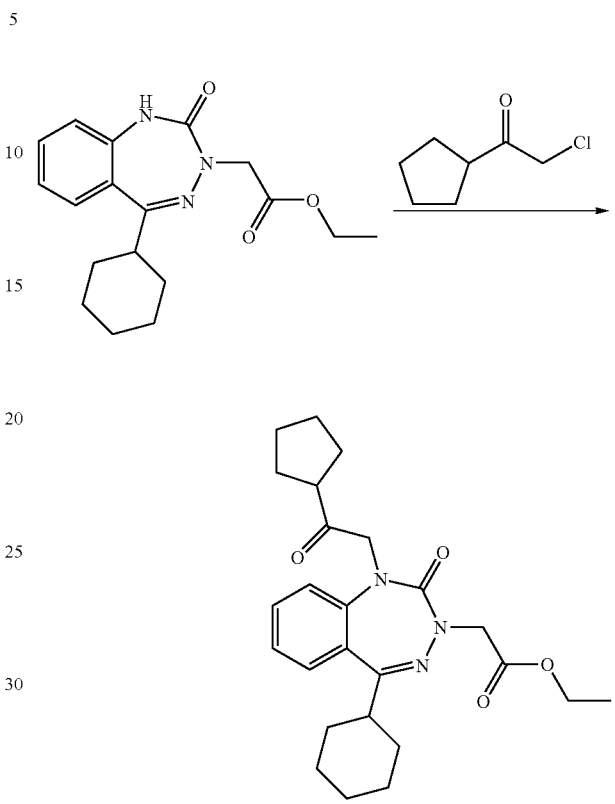

acid; in an organic solvent; to yield (5-cyclohexyl-2-oxo-1, 2-dihydro-benzo[e][1,2,4]triazepin-3-yl)-acetic acid ethyl ester;

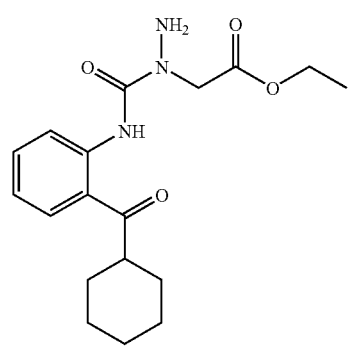

reacting the cyclohexyl-(2-isocyanato-phenyl)-methanone with ethyl hydrazine acetate hydrochloride; in the presence of an organic base; in an aprotic organic solvent; to yield [1-[[[2-(cyclohexylcarbonyl)-phenyl]-amino]-carbonyl]-hydrazino]-acetic acid ethyl ester;

reacting the (5-cyclohexyl-2-oxo-1,2-dihydro-benzo[e][1, 2,4]triazepin-3-yl)-acetic acid ethyl ester with 2-chloro-1-cyclopentyl-ethanone; in the presence of an organic or inorganic base; in an organic solvent; in the presence of a source of iodide; to yield [5-cyclohexyl-1-(2-cyclopentyl-2-oxo-ethyl)-2-oxo-1,2-dihydro-benzo[e][1,2,4]triazepin-3-yl]-acetic acid ethyl ester;

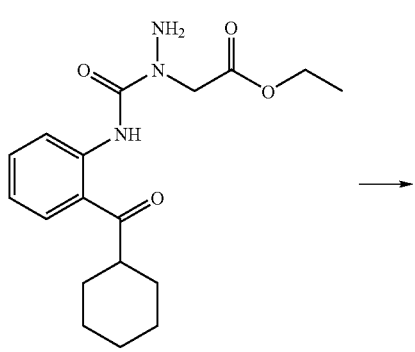

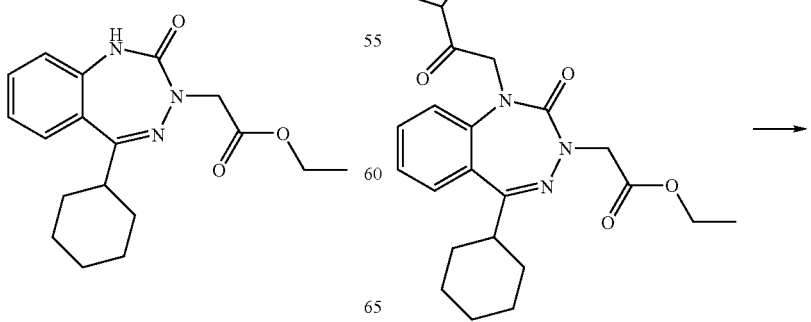

reacting the [1-[[[2-(cyclohexylcarbonyl)-phenyl]-amino]-carbonyl]-hydrazino]-acetic acid ethyl ester with an -continued

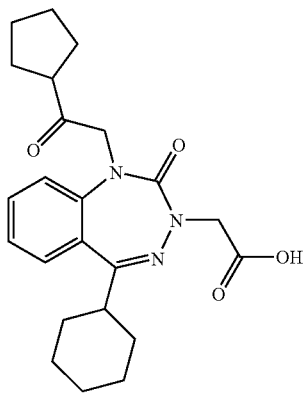

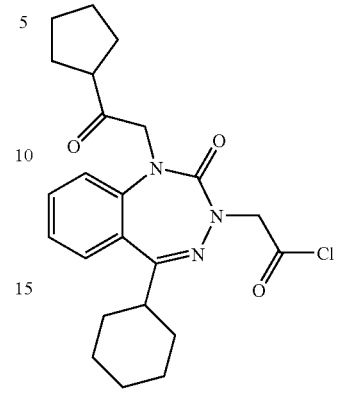

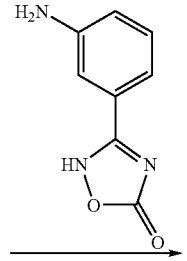

reacting the [5-cyclohexyl-1-(2-cyclopentyl-2-oxo-ethyl)-2-oxo-1,2-dihydro-benzo[e][1,2,4]triazepin-3-yl]-acetic acid ethyl ester with an aqueous base; to yield [5-cyclohexyl-1-(2-cyclopentyl-2-oxo-ethyl)-2-oxo-1,2-dihydro-benzo[e][1,2,4]triazepin-3-yl]-acetic acid;

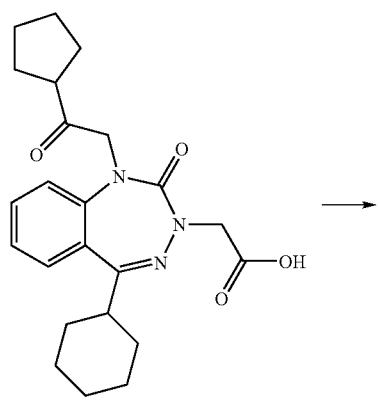

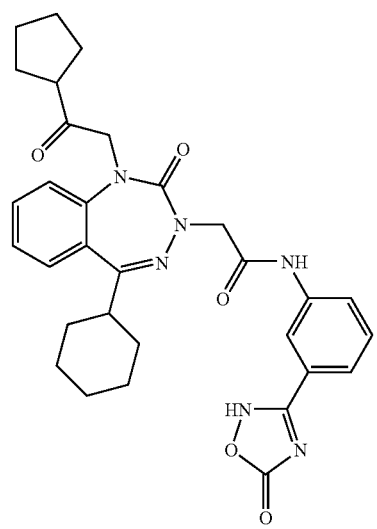

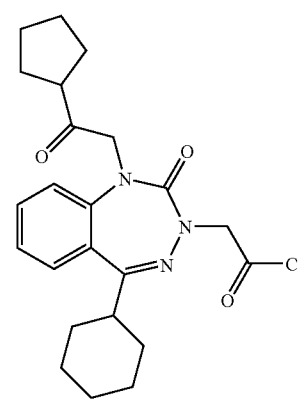

reacting the [5-cyclohexyl-1-(2-cyclopentyl-2-oxo-ethyl)-2-oxo-1,2-dihydro-benzo[e][1,2,4]triazepin-3-yl]-acetic acid with a chlorinating agent; in an organic solvent; to yield [5-cyclohexyl-1-(2-cyclopentyl-2-oxo-ethyl)-2-oxo-1,2-dihydro-benzo[e][1,2,4]triazepin-3-yl]-acetyl chloride;

reacting the [5-cyclohexyl-1-(2-cyclopentyl-2-oxo-ethyl)-2-oxo-1,2-dihydro-benzo[e][1,2,4]triazepin-3-yl]-acetyl chloride with 3-(3-amino-phenyl)-2H-[1,2,4]oxadiazol-5-one; in an aprotic organic solvent; to yield 2-[5-cyclohexyl-1-(2-cyclopentyl-2-oxo-ethyl)-2-oxo-1,2-dihydro-benzo[e][1,2,4]triazepin-3-yl]-N-[3-(5-oxo-2,5-dihydro-[1,2,4]oxadiazol-3-yl)-phenyl]-acetamide, the compound of formula (Is).

The present invention is further directed to processes for the preparation of intermediates in the synthesis of the compounds of formula (I), more specifically, compounds of formula (XIII), compounds of formula (XIV) and compounds of formula (XVI), as hereinafter described.

The present invention is further directed to a compound of formula (XIII) as hereinafter defined. In an embodiment, the compound of formula (XIII) is [1-[[[2-(cyclohexylcarbonyl)-phenyl]-amino]-carbonyl]-hydrazino]-acetic acid ethyl ester or a pharmaceutically acceptable salt thereof.

The present invention is further directed to a process for the preparation of 3-(3-amino-phenyl)-2H-[1,2,4]oxadiazol-5-one, a compound of the formula

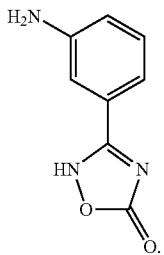

The present invention is further directed to a product prepared according to any of the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by a gastrin and/or cholecystokinin receptor (selected from the group consisting of gastrointestinal ulcers, dyspepsia, reflux oesophagitis (gastroesophageal reflux disease (GERD), both erosive and non-erosive), Zollinger-Ellison syndrome, Barrett's oesophagus (specialized intestinal metaplasi of distal oesophagus) ECL cell hyperplasoa, rebound hypersecretion (following cessation of anti-secretaro therapy) ECL-derived gastric polyps, cancers of the GI tract, more particularly in the stomach, oesophagus and colorectal areas, as well as tumors found in other organs such as the pancreas, lung (small cell lung carcinomas) and thyroid (thyroid medullary tumors), anxiety and potentiation of opiate induced analgesia) comprising administering to the subject in need thereof, a therapeutically effective amount of any of the compounds or pharmaceutical compositions described above.

Another example of the invention is the use of any of the compounds described herein in the preparation of a medicament for treating a disorder related to a gastrin and/or cholecystokinin receptor, as disclosed herein, in a subject in need thereof.

DETAILED DESCRIPTION OF THE INVENTION

The present invention is directed to a process for the preparation of compound of formula (X)

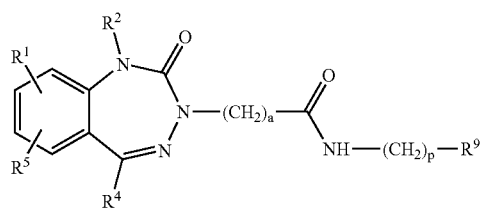

(I)

wherein $R^1$, $R^5$, $R^2$, $R^4$, a and $R^9$ are as herein defined. The compounds of formula (I) are benzotriazepine derivatives useful for the treatment of gastrin and cholecystokinin receptor mediate disorders, as disclosed in PCT publication WO 2003/041714.

The term "hydrocarbyl" is used herein to refer to monovalent groups consisting of carbon and hydrogen. Hydrocarbyl groups include alkyl, alkenyl and alkynyl groups (in both straight and branched chain forms), cycloalkyl (including polycycloalkyl groups such as bicyclooctyl and adamantyl), cycloalkenyl and aryl groups, and combination of the foregoing, such as alkylcyclalkyl, alkylpolycycloalkyl, alkylaryl, alkenylaryl, alkynylaryl, cycloalkylaryl and cycloalkenylaryl groups.

Where reference is made to a carbon atom of a hydrocarbyl group being replaced by a N, O or S atom, what is intended is that

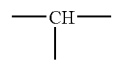

is replaced by

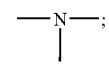

or that —$CH_2$— is replaced by —O— or —S—.

Where reference is made to an optionally substituted hydrocarbyl group, the hydrocarbyl group is substituted with 1, 2 or 3 groups independently selected from L-Q wherein:

L is a bond or a group of the formula —$(CR^{17}R^{18})_v$—Y—$(CR^{17}R^{18})_w$;

wherein v and w are independently 0, 1, 2, or 3; and

Y is a bond, —$CR^{15}$=$R^{16}$—, phenyl, furanyl, thiophenyl, pyrrolyl, thiazolyl, imidazolyl, oxazolyl, isoxazolyl, pyrazolyl, isoxazolonyl, piperazinyl, piperidinyl, morpholinyl, pyrrolidinyl, isothiazolyl, triazolyl, oxadiazzolyl, thidiazolyl, pyridyl or pyridazyl;

Q is H, ($C_1$ to $C_6$ alkyl)oxy, [N-Z]($C_1$ to $C_6$ alkyl)oxy($C_1$ to $C_6$ alkyl)amino, thio, ($C_1$ to $C_6$ alkyl)thio, carboxy($C_1$ to $C_6$ alkyl)thio, carbox, carboxy($C_1$ to $C_6$ alkyl), carboxy($C_1$ to $C_6$ alkenyl), [N-Z]carboxy($C_1$ to $C_6$ alkyl)amino, carboxy($C_1$ to $C_6$ alkyl)oxy, formyl, ($C_1$ to $C_6$ alkyl)carbonyl, ($C_1$ to $C_6$ alkyl)oxycarbonyl, ($C_1$ to $C_6$ alkyl)carbonyloxy, nitro, trihalomethyl, hydroxy, amino, [N-Z]($C_1$ to $C_6$ alkyl)aminocarbonyl, aminocarbonyl, ($C_1$ to $C_6$ alkyl)aminocarbonyl, di($C_1$ to $C_6$ alkyl)aminocarbonyl, [N-Z]($C_1$ to $C_6$ alkyl)carbonylamino, C5 to C8 cycloalkyl, [N-Z]($C_1$ to $C_6$ alkyl)carbonyl ($C_1$ to $C_6$ alkyl)amino, halo, halo($C_1$ to $C_6$ alkyl), sulfamoyl, [N-Z]($C_1$ to $C_6$ alkyl)sulfonylamino, ($C_1$ to $C_6$ alkyl)sulfonylaminocarbonyl, carboxy($C_1$ to $C_6$ alkyl)sulfonyl, carboxy ($C_1$ to $C_6$ alkyl)sulfinyl, tetrazolyl, [N-Z]tetrazolylamino, cyano, amidino, amidinothio, $SO_3H$, formyloxy, formamido, $C_3$ to $C_8$ cycloalkyl, ($C_1$ to $C_6$ alkyl)sulphamoyl, di($C_1$ to $C_6$ alkyl)sulphamoyl, ($C_1$ to $C_6$ alkyl)carbonylaminosulfonyl, 5-oxo-2,5-dihydro[1,2,4]oxadiazolyl, carboxy($C_1$ to $C_6$ alkyl)carbonylamino, tetrazolyl($C_1$ to $C_6$ alkyl), thio, [N-Z]tetrazolyl($C_1$ to $C_6$ alkyl)amino, 5-oxo-2,5-dihydro-[1,2,4]thidiazolyl, 5-oxo-1,2-dihydro[1,2,4]triazolyl, [N-Z]($C_1$ to $C_6$ alkyl)amino($C_1$ to $C_6$ alkyl)amino, or a group of the formula

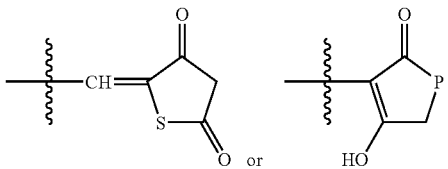

wherein P is O, S of NR$^{19}$; and Z is H, $C_1$ to $C_6$ alkyl, t-butoxycarbonyl, acetyl, benzoyl or benzyl;

$R^{15}$, $R^{17}$, $R^{18}$ and $R^{19}$ are independently H or $C_1$ to $C_3$ alkyl; and $R^{16}$ is H, $C_1$ to $C_3$ alkyl or acetylamino.

The prefix [N-Z] refers to possible substitutions of an amino group in the following compound or substitutent name. For example, [N-Z]alkylamino refers to groups of the form

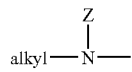

Similarly, [N-Z]tetrazolylamino, wherein Z is $C_1$ to $C_5$ alkyl, includes groups such as tetrazolyl([N-methyl]amino and tetrazolyl[N-ethyl]amino. Of course, when Z is H, no substitution is present.

The term "halogen" or "halo" is used herein to refer to any fluorine, chlorine, bromine or iodine. Most usually, however, halogen substituents in the compounds of the invention are chlorine and fluorine substituents. Groups such as halo($C_1$ to $C_6$ alkyl) includes mono-, di- or tri-halo substituted $C_1$ to $C_6$ alkyl groups. Moreover, the halo substitution may be at any position in the alkyl chain.

The term "alkyl" is used herein to refer to both straight and branched chain forms. Further, the alkyl chain may include multiple bonds. Hence the term "alkyl" also encompasses alkenyl and alkynyl groups. Likewise, the term "cycloalkyl" also encompasses cycloalkenyl groups. Preferably, alkyl and cycloalkyl groups as used in the present invention do not contain multiple bonds. Where there are preferred alkenyl groups, these are specified as alkenyl groups. However, specific reference to alkenyl groups is not to be construed as any limitation on the definition of alkyl groups described above.

Wherein reference is made to dialkyl groups [e.g. di($C_1$ to $C_6$ alkyl)amino groups], it is understood that the two alkyl groups may be the same or different.

In the interest of simplicity, terms which are normally used to refer to monovalent groups (such as "alkyl" or "phenyl") are also used herein to refer to divalent bridging groups, which are formed from the corresponding monovalent group by loss of one hydrogen atom. Whether such as term refers to a monovalent group or to a divalent group will be clear from the context. For example, when L is —$(CR^{17}R^{18})_v$—Y—$(CR^{17}R^{18})_w$—, it is clear that Y must be a divalent group. Thus when Y is defined as thiazolyl, for example, this refers to a divalent group having the structure

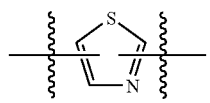

Where, as in this example, a divalent bridging group is formed from a cyclic moiety, the linking bonds may be on any suitable ring atom, subject to the normal rules of valency. Accordingly, by way of further example, the term pyrrolyl in the definition of Y includes all of the following groups:

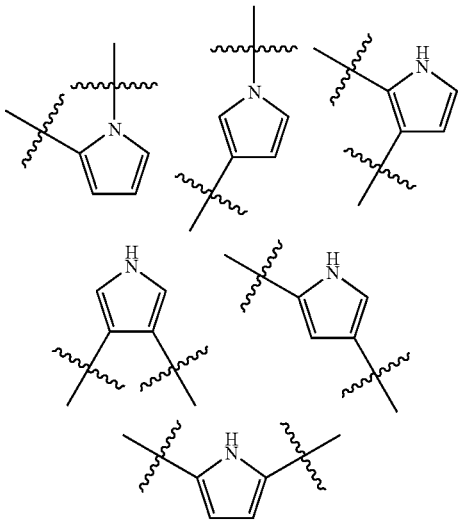

When a particular group is "substituted", that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "aprotic solvent" shall mean any solvent that does not yield a proton. Suitable examples include, but are not limited to DMF, dioxane, THF, acetonitrile, pyridine, dichloroethane, dichloromethane, MTBE, toluene, and the like.

As used herein, unless otherwise noted, the term "leaving group" shall mean a charged or uncharged atom or group, which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)-R' wherein R' is for example methyl, phenyl, trifluoromethyl, and the like; N-sulfonyl derivatives—groups of the formula —$SO_2$-R" wherein R" is for example tolyl, phenyl, trifluoromethyl, 2,2,5,7,8-pentamethylchroman-6-yl-, 2,3,6-trimethyl-4- methoxybenzene, and the like. Other suitable nitrogen protecting groups may be found in texts such as T. W. Greene & P. G. M. Wuts, *Protective Groups in Organic Synthesis*, John Wiley & Sons, 1991.

Abbreviations used in the specification, particularly the Schemes and Examples, are as follows:

BOC or Boc=t-Butoxy-carbonyl
$^{13}$C NMR=Carbon 13 Nuclear Magnetic Resonance
DCM=Dichloromethane
DIPEA=Diisopropylethylamine
DMAC=N,N-Dimethyacetamide
DMAP=4-N,N-Dimethylaminopyridine
DMF=N,N-Dimethylformamide
DMSO=Dimethylsulfoxide
EtOAc=EtOAc
EtOH=EtOH
$^{1}$H NMR=Hydrogen Nuclear Magnetic Resonance
HPLC=High Pressure Liquid Chromatography
GC=Gas Chromatgraphy
MeCN=Acetonitrile
MeOH=Methanol
m.p.=Melting Point
MTBE=Methyl t-butyl ether
PTSA=p-Toluenesulfonic acid (or Tosic acid)
TBAI=Tetra-n-butylammonium iodide
t-BOC or Boc=Tert-Butoxycarbonyl
TEA=Triethylamine
TFA=Trifluoroacetic Acid
THF=Tetrahydrofuran
TLC=Thin Layer Chromatography The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The present invention is directed to a process for the preparation of compounds of formula (I), as described in more detail in Scheme 1, below.

Scheme 1

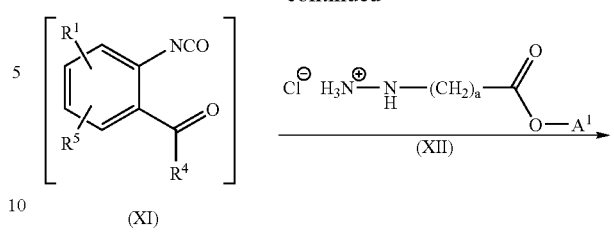

-continued

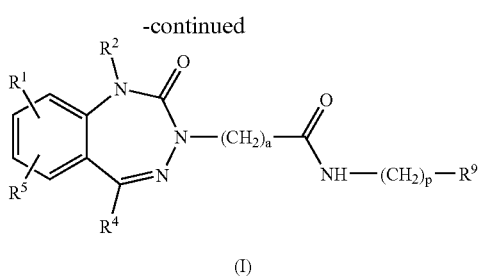

(I)

Accordingly, a suitably substituted compound of formula (X), a known compound or compound prepared by known methods, is reacted with phosgene or a phosgene equivalent such as diphosgene, triphosgene (also known as carbonic acid ditrichloromethyl ester), and the like, a known compound; in the presence of an organic base such as TEA, DIPEA, and the like, preferably, TEA; wherein the base is preferably present in an amount equal to about 1 equivalent; in an aprotic organic solvent such as DCM, toluene, THF, MTBE, and the like, preferably toluene; preferably at a temperature in the range of from −50° C. to about room temperature, more preferably, at a temperature in the range of from about −10° C. to about 0° C., to yield the corresponding compound of formula (XI), which is preferably not isolated.

The compound of formula (XI) is reacted with a suitably substituted compound of formula (XII), wherein $A^1$ is $C_{1-4}$alkyl, a known compound or compound prepared by known methods; in the presence of an organic base such as TEA, DIPEA, and the like, preferably, TEA; wherein the base is preferable present in an amount equal to about 1 equivalent; in an aprotic organic solvent such as DCM, toluene, THF, MTBE, and the like, preferably toluene; to yield the corresponding compound of formula (XIII). Preferably, the compound of formula (XIII) is isolated and optionally purified according to known methods.

The compound of formula (XIII) is reacted with an acid such as TFA, acetic acid, formic acid, PTSA, sulfuric acid, and the like, preferably an organic acid, more preferably, TFA; in an organic solvent such as toluene, MTBE, DCM, and the like, preferably toluene; to yield the corresponding compound of formula (XIV). One skilled in the art will recognize the selected acid may also act as the organic solvent for the reaction.

The compound of formula (XIV) is reacted with a suitable substituted compound of formula (XV), wherein $L^1$ is a suitable leaving group, a known compound or compound prepared by known methods; in the presence of a organic or inorganic base, such as TEA, DIPEA, pyridine, $Cs_2CO_3$, $K_2CO_3$, potassium t-butoxide, sodium t-butoxide, and the like, preferably an inorganic base, more preferably, $K_2CO_3$; wherein the base is preferably present in an amount greater than about 1 equivalent; in an organic solvent such as THF, DMF, DMAC, and the like; provided that when the leaving group is chloro, a source of iodide such as TBAI, NaI, and the like, preferably TBAI, is present; preferably, the source of iodide is present in an amount equal to about 1 equivalent; to yield the corresponding compound of formula (XVI), which is preferably not isolated.

The compound of formula (XVI) is reacted with an aqueous base such as NaOH, KOH, and the like, according to known methods, to yield the corresponding compound of formula (XVII). The compound of formula (XVII) is preferably isolated, according to known methods.

The compound of formula (XVII) is reacted with a suitably selected chlorinating agent such as thionyl chloride, oxalyl chloride, and the like, preferably thionyl chloride; according to known methods; to yield the corresponding compound of formula (XVIII).

The compound of formula (XVIII) is reacted with a suitably substituted compound of formula (XIX), a known compound or compound prepared by known methods, wherein the compound of formula (XIX) may be present as a free base or, for example, as its corresponding HCl salt; in the presence of an organic base such as TEA, DIPEA, pyridine, and the like, preferably DIPEA; wherein the base is preferably present in an amount from about 1 to about 2 equivalents; in an aprotic organic solvent such as acetonitrile, toluene, THF, MTBE, and the like, preferably acetonitrile; to yield the corresponding compound of formula (1).

One skilled in the art will recognize that the transformation of the carboxylic acid on the compound of formula (XVII) to the corresponding acid chloride on the compound of formula (XVIII) is preferably completed in situ, and the compound of formula (XVIII) is then reacted with the compound of formula (XIX) within the same reaction vessel.

The present invention is further directed to a process for the preparation of the compound of formula (Is) as described in more detail in Scheme 2, below.

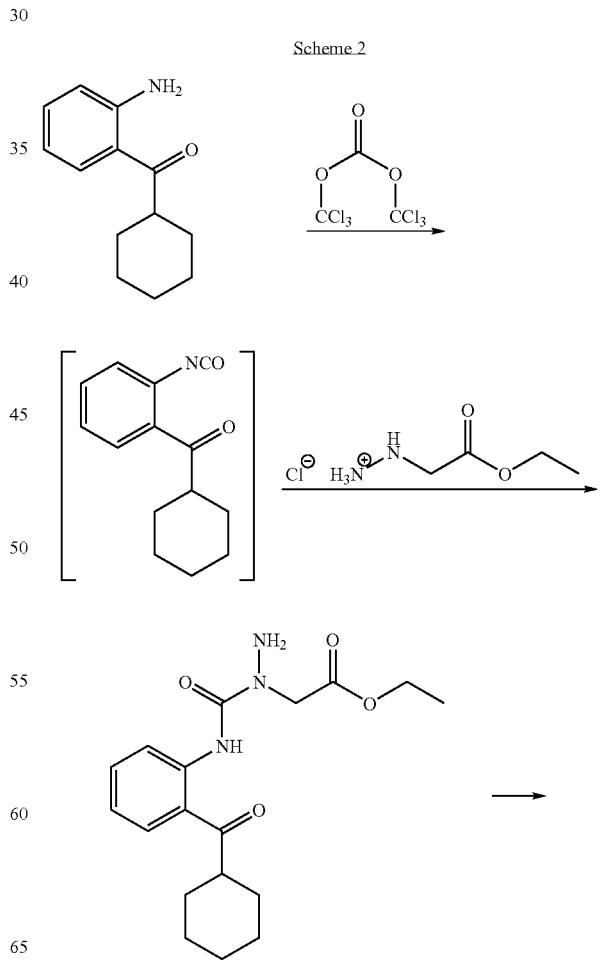

Scheme 2

-continued

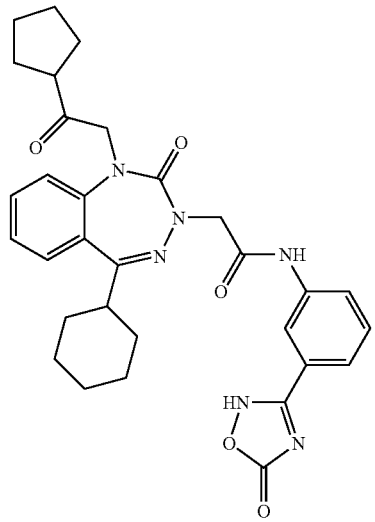

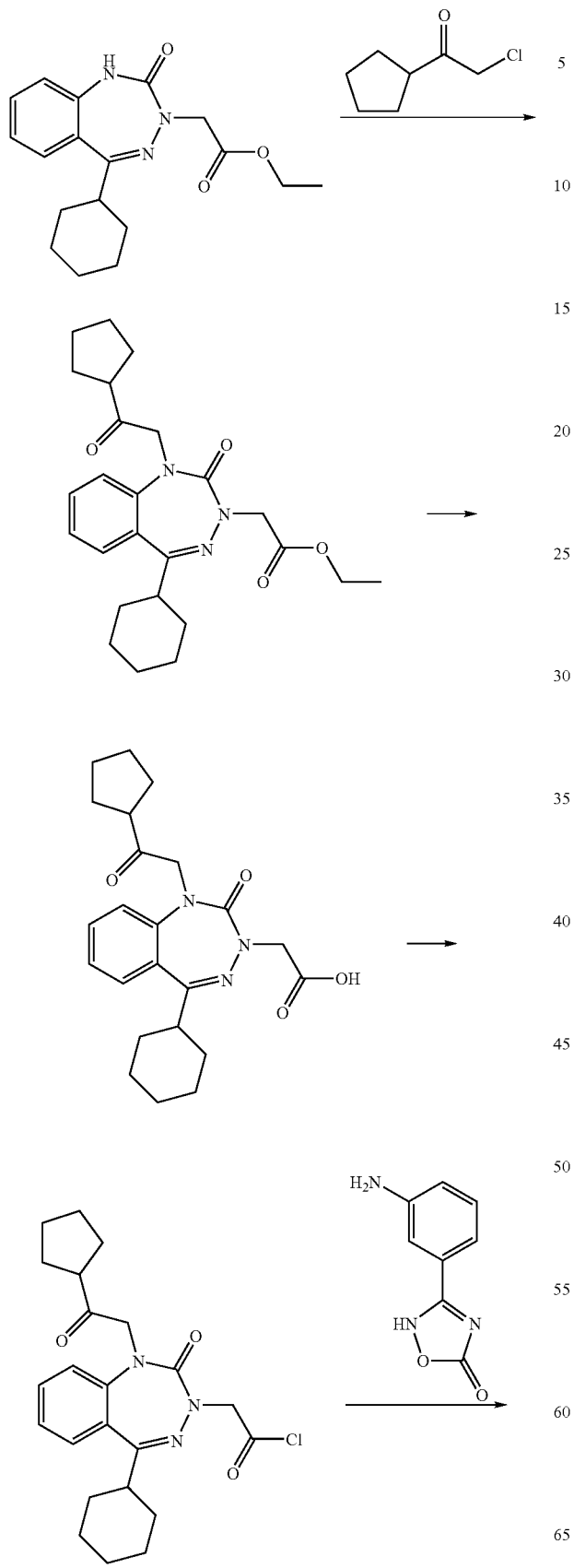

Accordingly, (2-amino-phenyl)-cyclohexyl-methanone, a known compound or compound prepared by known methods, is reacted with phosgene or a phosgene equivalent such as diphosgene, triphosgene (also known as carbonic acid ditrichloromethyl ester), and the like, a known compound; in the presence of an organic base such as TEA, DIPEA, and the like, preferably, TEA; wherein the base is preferably present in an amount equal to about 1 equivalent; in an aprotic organic solvent such as DCM, toluene, THF, MTBE, and the like, preferably toluene; preferably at a temperature in the range of from −50° C. to about room temperature, more preferably, at a temperature in the range of from about −10° C. to about 0° C., to yield cyclohexyl-(2-isocyanato-phenyl)-methanone, which is preferably not isolated.

The cyclohexyl-(2-isocyanato-phenyl)-methanone is reacted with ethyl hydrazine acetate hydrochloride, a known compound or compound prepared by known methods; in the presence of an organic base such as TEA, DIPEA, and the like, preferably, TEA; wherein the base is preferable present in an amount equal to about 1 equivalent; in an aprotic organic solvent such as DCM, toluene, THF, MTBE, and the like, preferably toluene; to yield [1-[[[2-(cyclohexylcarbonyl)-phenyl]-amino]-carbonyl]-hydrazino]-acetic acid ethyl ester, which is preferably isolated and optionally purified according to known methods.

The [1-[[[2-(cyclohexylcarbonyl)-phenyl]-amino]-carbonyl]-hydrazino]-acetic acid ethyl ester is reacted with an acid such as TFA, acetic acid, formic acid, PTSA, sulfuric acid, and the like, preferably an organic acid, more preferably, TFA; in an organic solvent such as toluene, MTBE, DCM, and the like, preferably toluene; to yield (5-cyclohexyl-2-oxo-1,2-dihydro-benzo[e][1,2,4]triazepin-3-yl)-acetic acid ethyl ester. One skilled in the art will recognize that the selected acid may also act as the organic solvent for the reaction.

The (5-cyclohexyl-2-oxo-1,2-dihydro-benzo[e][1,2,4]tri-azepin-3-yl)-acetic acid ethyl ester is reacted with 2-chloro-1-cyclopentyl-ethanone, a known compound or compound prepared by known methods; in the presence of a organic or inorganic base, such as TEA, DIPEA, pyridine, $Cs_2CO_3$, $K_2CO_3$, potassium t-butoxide, sodium t-butoxide, and the like, preferably an inorganic base, more preferably, $K_2CO_3$; wherein the base is preferably present in an amount greater than about 1 equivalent; in an organic solvent such as THF, DMF, DMAC, and the like; provided that when the leaving group is chloro, a source of iodide such as TBAI, NaI, and the like, preferably TBAI is present; preferably, the source of iodide is present in an amount equal to about 1 equivalent; to yield [5-cyclohexyl-1-(2-cyclopentyl-2-oxo-ethyl)-2-oxo-1, 2-dihydro-benzo[e][1,2,4]triazepin-3-yl]-acetic acid ethyl ester, which is preferably not isolated.

The [5-cyclohexyl-1-(2-cyclopentyl-2-oxo-ethyl)-2-oxo-1,2-dihydro-benzo[e][1,2,4]triazepin-3-yl]-acetic acid ethyl ester is reacted with an aqueous base such as NaOH, KOH, and the like, according to known methods, to yield [5-cyclohexyl-1-(2-cyclopentyl-2-oxo-ethyl )-2-oxo-1,2-dihydro-benzo[e][1,2,4]triazepin-3-yl]-acetic acid, which is preferably isolated, according to known methods.

The [5-cyclohexyl-1-(2-cyclopentyl-2-oxo-ethyl)-2-oxo-1,2-dihydro-benzo[e][1,2,4]triazepin-3-yl]-acetic acid is reacted with a suitably selected chlorinating agent such as thionyl chloride, oxalyl chloride, and the like, preferably thionyl chloride; according to known methods; to yield [5-cyclohexyl-1-(2-cyclopentyl-2-oxo-ethyl)-2-oxo-1,2-dihydro-benzo[e][1,2,4]triazepin-3-yl]-acetyl chloride.

The [5-cyclohexyl-1-(2-cyclopentyl-2-oxo-ethyl)-2-oxo-1,2-dihydro-benzo[e][1,2,4]triazepin-3-yl]-acetyl chloride is reacted with 3-(3-amino-phenyl)-2H-[1,2,4]oxadiazol-5-one, a known compound or compound prepared by known methods, wherein the 3-(3-amino-phenyl)-2H-[1,2,4]oxadiazol-5-one may be present as a free base or, for example, as its corresponding HCl salt; in the presence of an organic base such as TEA, DIPEA, pyridine, and the like, preferably DIPEA; wherein the base is preferably present in an amount from about 1 to about 2 equivalents; in an aprotic organic solvent such as acetonitrile, toluene, THF, MTBE, and the like, preferably acetonitrile; to yield the 2-[5-cyclohexyl-1-(2-cyclopentyl-2-oxo-ethyl)-2-oxo-1,2-dihydro-benzo[e][1, 2,4]triazepin-3-yl]-N-[3-(5-oxo-2,5-dihydro-[1,2,4]oxadiazol-3-yl)-phenyl]-acetamide, the compound of formula (Is).

Preferably, the [5-cyclohexyl-1-(2-cyclopentyl-2-oxoethyl)-2-oxo-1,2-dihydro-benzo[e][1,2,4]triazepin-3-yl]-acetic acid is reacted with thionyl chloride in situ, in an organic solvent such as acetonitrile, THF, MTBE, and the like, preferably acetonitrile; and then reacted with 3-(3-amino-phenyl)-2H-[1,2,4]oxadiazol-5-one as its corresponding HCl salt, in the presence of an organic base such as TEA, DIPEA, pyridine, and the like, preferably DIPEA; wherein the base is preferably present in an amount greater than or equal to about 2 equivalents; in the same organic solvent; to yield the 2-[5-cyclohexyl-1-(2-cyclopentyl-2-oxo-ethyl )-2-oxo-1,2-dihydro-benzo[e][1,2,4]triazepin-3-yl]-N-[3-(5-oxo-2,5-dihydro-[1,2,4]oxadiazol-3-yl)-phenyl]-acetamide, the compound of formula (Is).

One skilled in the art will recognize that in the reaction of the compound of formula (XI) with phosgene or a source of phosgene, substituent groups which terminate with a proton source such as OH, SH, NH, $NH_2$, and the like, are preferably protected and then de-protected at a later time to prevent by-products and side reactions with these groups.

The present invention is further directed to a process for the preparation of 3-(3-amino-phenyl)-2H-[1,2,4]oxadiazol-5-one, a compound of the formula

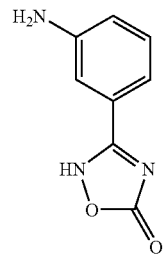

as described in more detail in the Examples which follow herein. Briefly, 3-(3-amino-phenyl)-2H-[1,2,4]oxadiazol-5-one may be prepared according to the process outlined in Scheme 3, below.

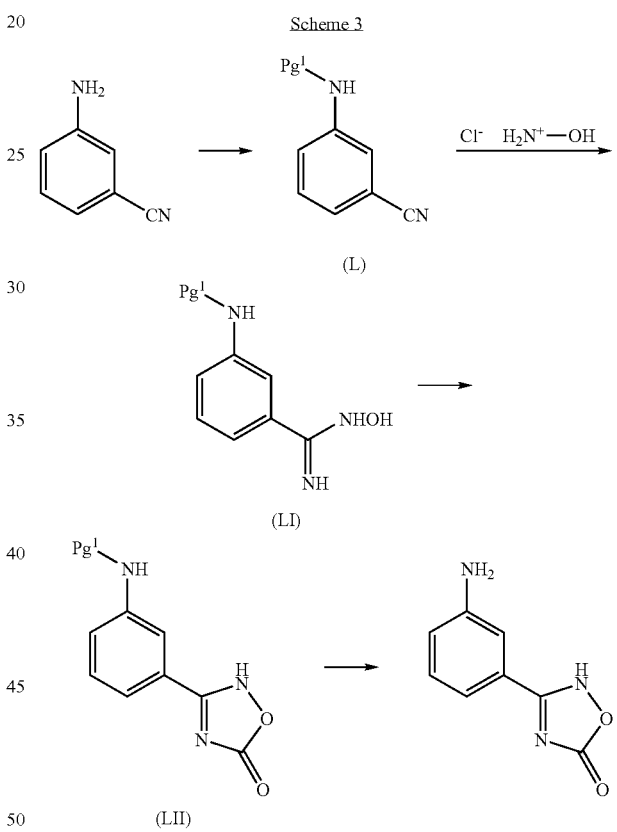

Accordingly, 2-amino-benzonitrile, a known compound, is protected, according to known methods, to yield the corresponding compound of formula (L) wherein $Pg^1$ is a suitable nitrogen protecting group such as BOC.

The compound of formula (L) is reacted with hydroxylamine hydrochloride, a known compound, in an organic solvent such as an alcohol, preferably ethanol, to yield the corresponding compound of formula (LI).

The compound of formula (LI) is reacted with 1,1,-carbonyldiimidazole, a known compound, in an organic solvent such as THF, to yield the corresponding compound of formula (LII).

The compound of formula (LII) is de-protected according to known methods, for example by reacting with an acid such as HCl, and the like, to yield 3-(3-amino-phenyl)-2H-[1,2,4]oxadiazol-5-one, as its corresponding salt.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at a diastereomeric excess of greater than or equal to about 80%, more preferably, at a diastereomeric excess of greater than or equal to about 90%, more preferably still, at a diastereomeric excess of greater than or equal to about 95%, more preferably still, at a diastereomeric excess of greater than or equal to about 98%, most preferably, at a diastereomeric excess of greater than or equal to about 99%.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diEtOHamine, diethylamine, 2-(diethylamino)-EtOH, EtOHamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triEtOHamine, tromethamine and zinc hydroxide.

The present invention further comprises pharmaceutical compositions containing one or more compounds of formula (I), with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg and may be given at a dosage of from about 0.001-5000 mg/day, preferably from about 1-1000 mfg/day, more preferably from about 10-200 mg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating a disorder related to a gastrin and/or cholecystokinin receptor described in the present invention may also be carried out using a pharmaceutical composition comprising any of the compounds as defined herein and a pharmaceutically acceptable carrier. The pharmaceutical composition may contain between about 0.1 mg and 1000 mg, preferably about 1 to 500 mg, more preferably about 5 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as EtOH, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrol idone, pyran copolymer, polyhydroxypropylmethacrylam idephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders related to a gastrin and/or cholecystokinin receptor is required.

The daily dosage of the products may be varied over a wide range from 0.001 to 5,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 µg/kg to about 50 mg/kg of body weight per day, preferably, the range is from about 10 µg/kg to about 10 mg/kg of body weight per day, more preferably, from about 100 µg/kg to about 2.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

[3-(2-Cyclohexanecarbonyl-phenyl)-1-amino-ureido]-acetic acid ethyl ester

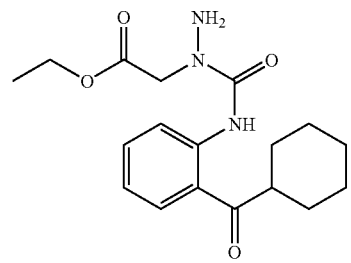

A solution of (2-amino-phenyl)-cyclohexyl-methanone (1.0 g, 5 mmol) in DCM (15 mL) was charged with triethylamine (3.6 mL) and cooled to −50° C. While at this temperature, a solution of triphosgene (also known as carbonic acid ditrichloromethyl ester) (0.5 g) in DCM (5 mL) was added at once and the temperature was observed to increase to −10° C. The resulting solution was aged at between −10° C. and −20° C. for a period of about 15 min and then transferred slowly via syringe to a flask containing a slurry of ethyl hydrazino acetate hydrochloride (0.5 g, 3.2 mmol), and triethylamine (1 mL) in DCM (10 mL). During the addition the temperature was observed to increase from 23° C. to 26° C. The reaction mixture was aged at ambient temperature for 2 hours and then filtered to remove the insolubles (triethylamine hydrochloride). The filtrate was concentrated under vacuum and the resulting residue dissolved in isopropyl acetate (10 mL). The solution was washed with water (5 mL), brine (10 mL), and the solvent exchanged with methyl t-butyl ether (5 mL). The resulting solution was then diluted with heptane (25 mL) and aged overnight, over which time a precipitated formed. The solid was removed and air-dried to yield [1-[[[2-(cyclohexylcarbonyl)phenyl]amino]carbonyl]hydrazino]-acetic acid ethyl ester as a solid, with structure confirmed by spectroscopic means.

m.p. 108-110° C. $^1$H NMR (CDCl$_3$): 12.37(1H,s) 8.69 (1H, d, J=3.1Hz); 7.90 (1H, d, J=2.9Hz), 7.49 (1H, t, J=2.9Hz), 7.05 (1H, t, J=3.0Hz), 4.41 (2H, s), 4.25 (2H, q J=3.2Hz),4.21 (2H, s), 3.37 (1H, m), 1.82 (4H, m), 1.81-1.32 (6 H. m), 1.29 (3H, t, J=3.2) $^{13}$C NMR (CDCl$_3$): 207.64, 165.85, 142.16, 134.29, 130.35, 121.18, 120.74, 119.99, 61.37, 51.16, 46.72, 29.88, 25.98, 25.94, 14.20

EXAMPLE 2

(5-Cyclohexyl-2-oxo-1,2-dihydro-benzo[e][1,2,4]triazepin-3-yl)-acetic acid ethyl ester

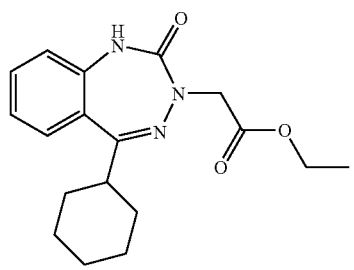

[1-[[[2-(Cyclohexylcarbonyl)phenyl]amino]carbonyl]hydrazino]-acetic acid ethyl ester (20 mg) was dissolved in TFA (0.2 mL) and aged for about 15 min. HPLC analysis at this point revealed the disappearance of the signal @ 10.5 min corresponding to starting material, and the appearance of a signal @ 11.01 min corresponding to product. This material was characterized by comparison of the HPLC traces with that of an authentic sample.

EXAMPLE 3

(5-Cyclohexyl-2-oxo-1,2-dihydro-benzo[e][1,2,4]triazepin-3-yl)-acetic acid ethyl ester

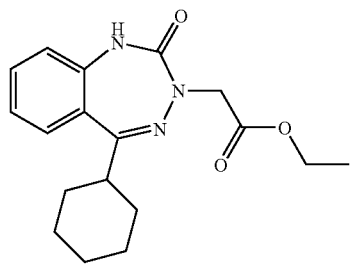

To a cold solution of triphosgene (1.2 g, 4 mmol) in toluene (10 mL) was added slowly a solution of (2-amino-phenyl)-cyclohexyl-methanone (2.4 g) and triethylamine (3.3 ml) in toluene (16 mL). The mixture was then warmed up to 20-23° C. and aged for a period of about 1 hr under stirring. The resulting slurry was then added slowly to a warm (60° C.) mixture of ethyl hydrazine-acetate hydrochloride (1.8 g) and triethylamine (1.4 g) in toluene (20 mL). The reaction mixture was aged at 60° C. for about 20 m in and then heated to about 100° C. While at this temperature, trifluoroacetic acid (0.5 mL) was added and the reaction mixture was aged until the cyclization was completed (approximately 10 min). The reaction mixture was then cooled to about 20-23° C. and filtered. The filtrate was washed with 1N HCl (10 mL), water (10 mL), brine (10 mL) and then evaporated to a residue. The residue (5.2 g) was dissolved in methyl t-butyl ether (10 mL), and then heptane (~50 mL) was slowly added. The product which precipitated out of the solution, was collected by filtration and dried to yield (5-cyclohexyl-2-oxo-1,2-dihydro-benzo[e][1,2,4]triazepin-3-yl)-acetic acid ethyl ester as an off-white solid.

The product was confirmed by HPLC with authentic material used as a reference.

EXAMPLE 4

[5-cyclohexyl-1-(2-cyclopentyl-2-oxo-ethyl)-2-oxo-1,2-dihydro-benzo[e][1,2,4]triazepin-3-yl]-acetic acid ethyl ester

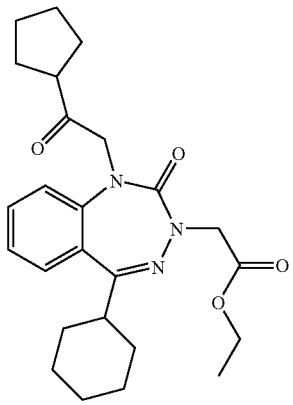

To a solution of (5-cyclohexyl-2-oxo-1,2-dihydro-benzo[e][1,2,4]triazepin-3-yl)-acetic acid ethyl ester (1.1 g) and 2-chloro-1-cyclopentylethanone (0.8 g) in THF (3 mL) was added slowly tetrabutylammonium iodide (1.2 g) and potassium t-butoxide in THF (5.5 mL). The resulting solution was stirred at 25° C. for 4 hrs, cooled to 20 to 23° C. and aged for about 15 hrs. HPLC analysis revealed a mixture of [5-cyclohexyl-1-(1-hydroxy-spiro[2.4]hept-1-yl)-2-oxo-1,2-dihydro-benzo[e][1,2,4]triazepin-3-yl]-acetic acid ethyl ester and a small amount of [5-Cyclohexyl-1-(1-hydroxy-spiro[2.4]hept-1-yl)-2-oxo-1,2-dihydro-benzo[e][1,2,4]triazepin-3-yl]-acetic acid ethyl ester (a by-product of the reaction) and starting material.

Note: When the above procedure was carried out in the absence of TBAI (a source of iodide) no product was obtained, instead only the [5-Cyclohexyl-1-(1-hydroxy-spiro[2.4]hept-1-yl)-2-oxo-1,2-dihydro-benzo[e][1,2,4]triazepin-3-yl]-acetic acid ethyl ester by-product and starting material were detected.

EXAMPLE 5

[5-Cyclohexyl-1-(2-cyclopentyl-2-oxo-ethyl)-2-oxo-1,2-dihydro-benzo[e][1,2,4]triazepin-3-yl]-acetic acid

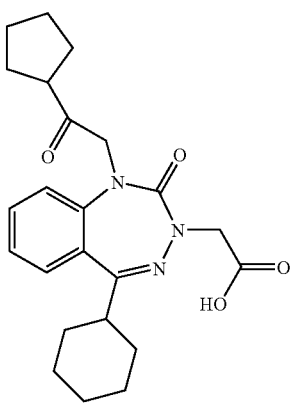

To a solution of (5-cyclohexyl-2-oxo-1,2-dihydro-benzo[e][1,2,4]triazepin-3-yl)-acetic acid ethyl ester (50 g, 151.7 mmol) in DMF (250 mL) was added potassium carbonate (325 mesh, 102 g, 738 mmol) and tetrabutylammonium iodide (46.0 g, 124.5 mmol). The resulting mixture was heated to about 50-55° C. and while at this temperature, 2-chloro-1-cyclopentylethanone (57.0 g, 373.5 mmol) was added drop-wise over a period of about 1 hr. The reaction mixture was then aged for 1 hr, cooled to ambient temperature and diluted with MTBE (50 mL). The inorganic solids were removed by filtration and rinsed with additional MTBE (50 mL). To the combined filtrates was added DMF (50 mL) and the resulting mixture was treated with 3N NaOH (150 mL), then stirred at −30° C. for about 1 hr. The reaction mixture was then again diluted with MTBE (100 mL) and the layers were separated. The aqueous layer was poured slowly under vigorous agitation, into another flask containing cold 2N HCl solution (400 mL) which was maintained at ~5° C. Isopropyl acetate (300 mL) was added to the reaction mixture and the layers were separated. The organic layer was rinsed with water (300 mL) and then diluted with n-heptane (300 mL), at which point a solid was observed to precipitate. The precipitate was filtered and dried under vacuum to constant weight to yield the title compound as an off-white solid.

The product was confirmed by HPLC with authentic material used as a reference.

EXAMPLE 6

2-Chloro-1-cyclopentyl-ethanone (Synthesis Adapted from Procedure as Disclosed by Tillyer at al. *Synlett*, 1996, (3), 225-226)

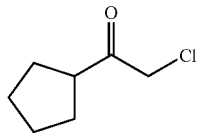

To a cold (~0° C.) solution of $K_2CO_3$ (31.2 g, 225 mmol, ) in water (125 mL) was added N, O-dimethylhydroxylamine hydrochloride (10 g, 100 mmol) and toluene (125 mL). The reaction mixture was further cooled to −5° C. and chloroacetyl chloride (10 mL, 125 mmol, )was added slowly under vigorous agitation. The reaction mixture was then warmed to ambient temperature over 45 min and analyzed by GC for completion. The layers were separated and the aqueous layer was extracted with toluene (3×50 mL). The combined organic layers were concentrated to a solid residue. The residue was dissolved in anhydrous THF (200 mL) cooled to ~0° C. To the reaction mixture was then added a solution of the cyclopentylmagnesium chloride (60 mL, 2M in diethyl ether), drop-wise, maintaining the temperature at less than about 5° C. The resulting solution was then warmed to ambient temperature over a period of ~1 hr and then slowly quenched into a cold 3N HCl (100 mL, ). The resulting mixture was then aged for ~30 min. The layers were separated and the aqueous layer extracted with MTBE (50 mL). The combined organic layers were washed with brine (50 mL), dried over $MgSO_4$ and concentrated to dryness to yield the title compound as a crude product, as a yellow liquid.

$^1$H NMR ($CDCl_3$) 4.19 (2H, s), 3.12 (1H, m), 1.93 -1.55 (8H, m)

EXAMPLE 7

2-[5-Cyclohexyl-1-(2-cyclopentyl-2-oxo-ethyl)-2-oxo-1,2-dihydro-benzo[e][1,2,4]triazepin-3-yl]-N-[3-(5-oxo-4,5-dihydro-[1,2,4]oxadiazol-3-yl)-phenyl]-acetamide

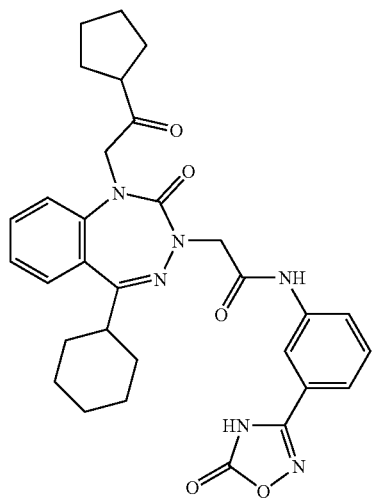

A 500 mL three-necked-reaction flask was charged with [5-cyclohexyl-1-(2-cyclopentyl-2-oxo-ethyl)-2-oxo-1,2-dihydro-benzo[e][1,2,4]triazepin-3-yl]-acetic acid (32.3 g, 78 mmol), DCM (150 mL) and a few drops of DMF. After cooling to 0° C., oxalyl chloride (8.9 mL, 102 mmol) was added by addition funnel and the mixture warmed to room temperature (over about 30 min). After this time the reaction mixture was concentrated to dryness, then charged with DCM (50 mL) and concentrated again. DCM (150 mL) was added and the reaction mixture cooled to 0° C. 3-(3-Amino-phenyl)-4H-[1,2,4]oxadiazol-5-one (14.6 g, 82 mmol) and DIPEA (41 mL, 235 mmol) in DCM (40 mL) were slowly added to the reaction by addition funnel. The reaction mixture was stirred at room temperature and monitored for starting material consumption (5 h). Upon completion, the reaction mixture was quenched with 2N HCl (140 mL), and washed with DCM (1×100 mL), then after phase separation the organic layer was washed with brine (1×100 mL). The organic layer was separated and dried ($Na_2SO_4$, 75 g), filtered and concentrated to yield a light yellow solid after high vacuum. The solid was crystallized from MeCN to yield the title compound as an off white solid.

EXAMPLE 8

2-[5-Cyclohexyl-1-(2-cyclopentyl-2-oxo-ethyl)-2-oxo-1,2-dihydro-benzo[e][1,2,4]triazepin-3-yl]-N-[3-(5-oxo-4,5-dihydro-[1,2,4]oxadiazol-3-yl)-phenyl]-acetamide

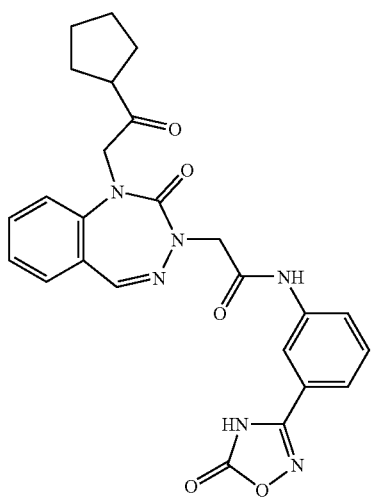

A 2L three-necked-reaction flask was charged with [5-cyclohexyl-1-(2-cyclopentyl-2-oxo-ethyl)-2-oxo-1,2-dihydro-benzo[e][1,2,4]triazepin-3-yl]-acetic acid (100 g, 243 mmol) and MeCN (600 mL). At room temperature SOCl₂ (19.5 mL, 267.3 mmol) was added via addition funnel. In a 3L three-necked-flask a slurry of 3-(3-amino-phenyl)-4H-[1,2,4]oxadiazol-5-one hydrochloride salt (53.47 g, 250.3 mmol) in MeCN (300 mL) was treated with DIPEA (148 mL, 851 mmol) at room temperature, then cooled to −10° C. The solution of the acid chloride was then added to the amine solution to maintain the temperature below −5° C. Upon consumption of starting material (30 minutes) the reaction mixture was quenched by addition of 1N HCl (650 mL) followed by addition of water (300 mL). The reaction mixture was allowed to warm to room temperature and stirred overnight. The resulting suspension was then cooled in an ice bath (1 h) and the solid collected by vacuum filtration and washed with MeCN (50 mL) to yield the title compound as an off white solid.

m.p.: 182° C.

The product was further confirmed by HPLC with authentic material used as a reference.

The product was confirmed by HPLC with authentic material used as a reference.

EXAMPLE 9

3-(3-{2-[5-Cyclohexyl-1-(2-cyclopentyl-2-oxo-ethyl)-2-oxo-1,2-dihydro-benzor[e][1,2,4]triazepin-3-yl]-acetylamino}-phenyl)-propionic acid ethyl ester

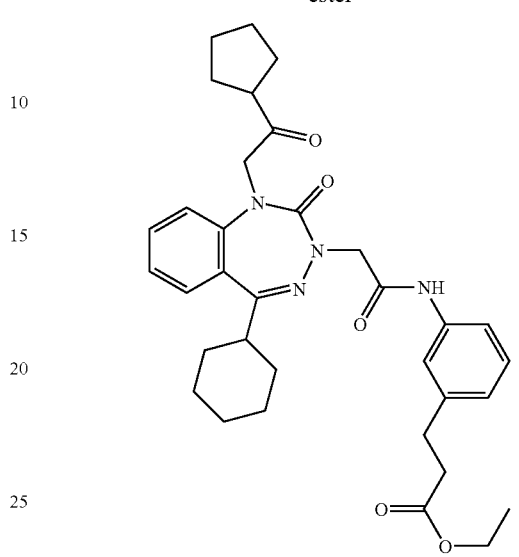

To a 1 L three-necked-reaction flask equipped with a magnetic stir bar, nitrogen outlet and addition funnel was charged [5-cyclohexyl-1 -(2-cyclopentyl-2-oxo-ethyl)-2-oxo-1,2-dihydro-benzo[e][1,2,4]triazepin-3-yl]-acetic acid (40.6 g, 99 mmol), 3-(3-amino-phenyl)-propionic acid ethyl ester hydrochloride (23.8 g, 104 mmol) and MeCN (220 mL). At room temperature, the off white slurry was treated with SOCl₂ (7.92 mL, 109 mmol) via addition funnel. Upon completion of addition the resulting solution was allowed to stir (1 hour). DIPEA (72.2 mL, 414 mmol) was then added slowly via addition funnel to the reaction. Upon consumption of starting material the reaction mixture was quenched by addition of water (300 mL). The resulting suspension was extracted with EtOAc (2×500 mL), the phases were separated and the organics dried (Na₂SO₄, 50 g), filtered and concentrated to yield a dark oil. The dark oil was taken up in warm MeOH (250 mL) and cooled to precipitate the title compound as a off white solid.

m.p.: 126° C. ¹H NMR (300 MHz, CDCl₃): δ8.25 (1H, s), 7.54-7.41 (2H, m), 7.34-7.24 (2H, m), 7.22-7.16 (2H, m), 7.05 (1H, d, J=8.4 Hz), 6.95-6.86 (1H, m), 4.79 (4H, s), 4.65 (1H, d, J=17.7 Hz), 4.53 (1H, d, J=18.0 Hz), 4.39 (1H, d, J=30.1Hz), 4.23 (1H, d, J=26.1Hz), 4.13 (2H, dd, J=14.3 Hz, 7.1Hz), 2.99-2.85 (2H, m), 2.59 (2H, dd, J=9.0 Hz, 8.4 Hz), 2.06-1.49 (14H, m), 1.37-1.17 (5H, m).

EXAMPLE 10

(3-Cyano-phenyl)-carbamic acid tert-butyl ester (See also PCT Publications WO/0075120, WO9319063A1 and WO9814451 A1)

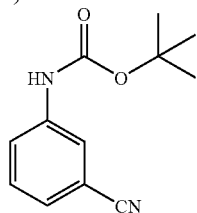

A 3L round bottom flask equipped with an overhead stirrer, 500 mL addition funnel, and nitrogen outlet was charged with 3-aminobenzonitrile (200 g, 1.69 mol) and EtOAc (500 mL). The resulting solution was treated with DMAP (20.6 g, 0.169 mol), followed by addition of pyridine (410 mL, 5.07 mol). Di-t-butyl dicarbonate (406 g, 1.86 mol) in EtOAc (300 mL) was then added via addition funnel. Upon consumption of starting material (2 h) the reaction mixture was quenched by addition of 2N HCl (750 mL, 1.5 mol) and allowed to stir (30 min). Using a separatory funnel the phases were separated and the organic phase washed with 2N HCl (2×500 mL) followed by a brine wash (500 mL). The organic layer was evaporated to dryness. The crude product was crystallized from EtOH to yield the title compound as a light brown solid.

m.p.: 130° C. $^1$H NMR (300 MHz, DMSO): δ 9.76 (1H, s), 7.89 (1H, s), 7.71 (1H, d, J=7.9 Hz), 7.48 (1H, t, J=7.9 Hz), 7.43 (1H, t, J=7.9 Hz), 1.48 (9H, s).

EXAMPLE 11

[3-(N-Hydroxycarbamimidoyl)-phenyl]-carbamic acid tert-butyl ester

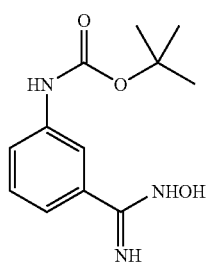

A 5 L round bottom flask equipped with an overhead stirrer, and 500 mL addition funnel was charged with 3-(t-butyloxycarbonylamino)benzonitrile (264.4 g, 1.21 mol), hydroxylamine hydrochloride (294.6 g, 4.24 mol) and 95% EtOH (1 L). The resulting suspension was treated with a solution of potassium carbonate (711.8 g, 5.15 mol) in water (1 L) and the suspension heated to 60° C. The reaction was followed by TLC and HPLC for starting material consumption to completion. The reaction mixture was then cooled to ambient temperature the organic layer was separated and concentrated to approximately 500 mL, then diluted with water (1 L). The resulting precipitate was collected by vacuum filtration and dried to yield the title compound as an off white solid.

m.p.: 176.4 C $^1$H NMR (300 MHz, DMSO) δ 9.59 (1H, s), 9.38 (1H, s), 7.83 (1H, s), 7.47-7.37 (1H, m), 7.29-7.19 (2H, m), 5.70 (1H, br s), 1.48 (9H, s).

EXAMPLE 12

[3-(5-Oxo-2,5-dihydro-[1,2,4]oxadiazol-3-yl)-phenyl]-carbamic acid tert-butyl ester

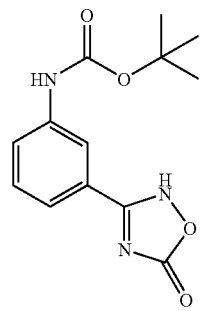

A 3 L round bottom flask equipped with an overhead stirrer and heating mantle was charged with 3-(t-butyloxycarbonylamino)benzenylamidoxime (251.3 g, 1 mol) and 1,1'-carbonyldiimidazole (2027 g, 1.25 mol) and dissolved in THF (1.9 L). The reaction mixture was then heated to reflux. Upon consumption of starting material, the reaction mixture was cooled to ambient temperature and concentrated under vacuum to ~300 mL. The reaction mixture was added to 2N HCl (1.5 L) and stirred to yield an off-white solid, crude product. The crude solid was crystallized from acetonitrile (1 L) to yield the title compound as an off white solid.

m.p: 193° C. $^1$H NMR (300 MHz, DMSO) δ 12.97 (1H, s), 9.66 (1H, s), 8.08 (1H, s), 7.58 (1H, d, J=8.4 Hz), 7.46 (1H, t, J=7.8 Hz), 7.36 (1H, d, J=7.2 Hz), 1.48 (9H, S).

EXAMPLE 13

3-(3-Amino-phenyl)-2H-[1,2,4]oxadiazol-5-one

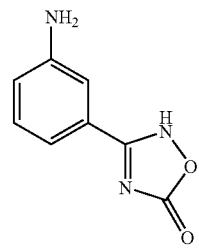

A 1 L flask equipped with a magnetic stir bar and heating mantle was charged with [3-(5-oxo-2,5-dihydro-[1,2,4]oxadiazol-3-yl)-phenyl]-carbamic acid tert-butyl ester (60.0 g, 0.22 mol) and EtOH (800 mL). The resulting suspension was then treated with HCl gas (31 g, 0.86 mol) at ambient temperature over 20 minutes. The reaction mixture was then heated to 60° C., until starting material was consumed (1.5 h). The reaction mixture was cooled in an ice-bath and the resulting solid was collected via vacuum filtration. The filter pad was washed with EtOH (75 mL) and air dried to yield the title compound as an off white solid.

m.p.: decomposition 240° C.; $^1$H NMR (300 MHz, DMSO) δ (1H, s), 7.69-7.55 (3H, m), 7.45 (1H, d, J=8.0Hz).

EXAMPLE 14

Pharmaceutical Composition

As a specific embodiment of an oral composition, 100 mg of the compound of formula (Is), prepared as described herein is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A process for the preparation of a compound of formula (Is)

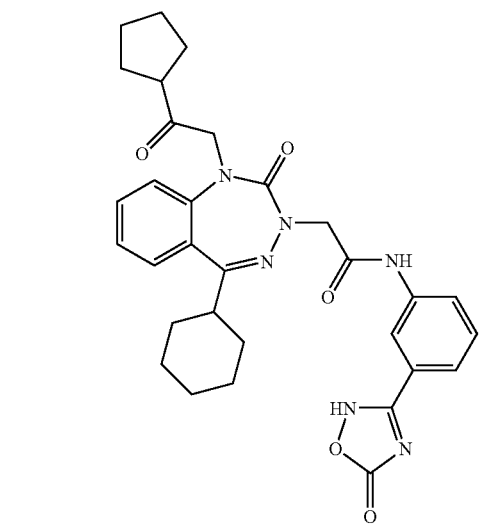

(Is)

comprising

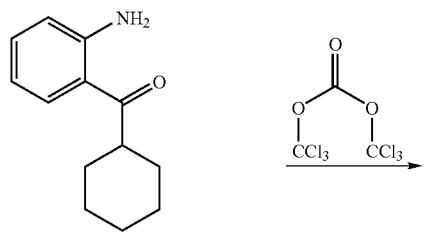

reacting (2-amino-phenyl)-cyclohexyl-methanone with phosgene, diphosgene or triphosgene; in the presence of an organic base; in an aprotic organic solvent; to yield cyclohexyl-(2-isocyanato-phenyl)-methanone;

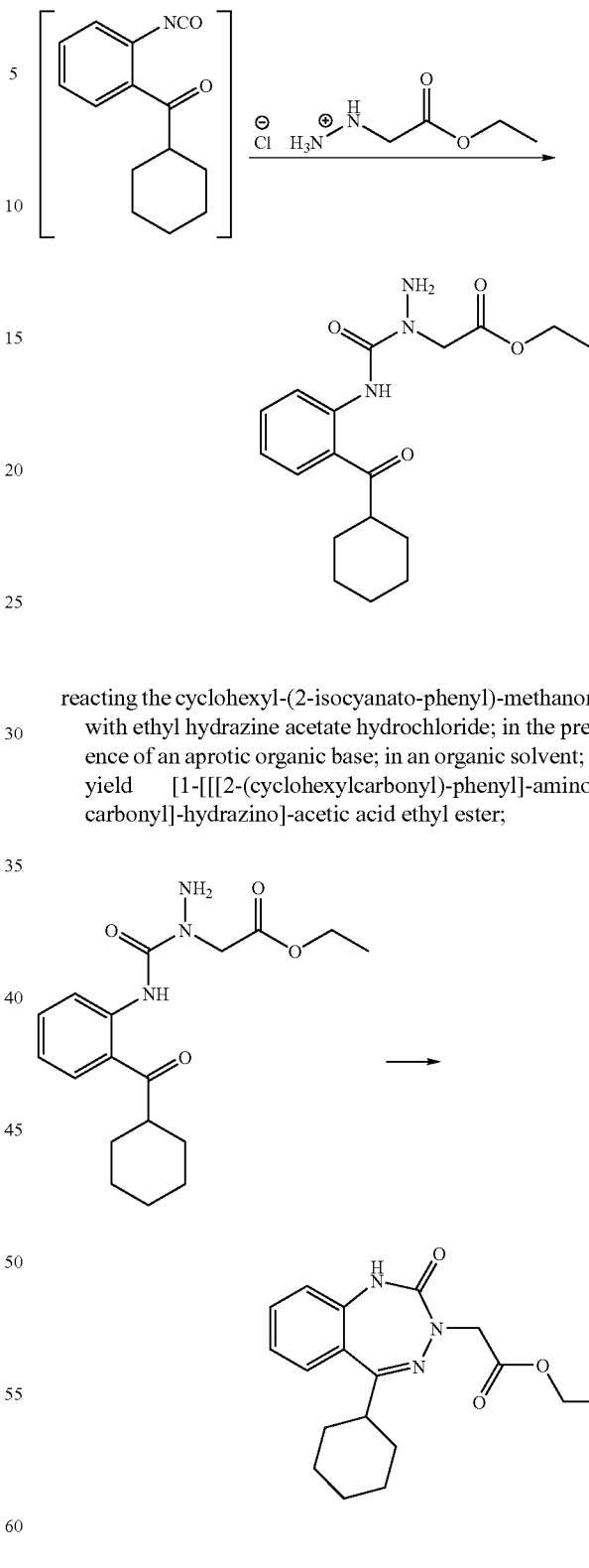

reacting the cyclohexyl-(2-isocyanato-phenyl)-methanone with ethyl hydrazine acetate hydrochloride; in the presence of an aprotic organic base; in an organic solvent; to yield [1-[[[2-(cyclohexylcarbonyl)-phenyl]-amino]-carbonyl]-hydrazino]-acetic acid ethyl ester;

reacting the [1-[[[2-(cyclohexylcarbonyl)-phenyl]-amino]-carbonyl]-hydrazino]-acetic acid ethyl ester with an acid; in an organic solvent; to yield (5-cyclohexyl-2-oxo-1,2-dihydro-benzo[e][1,2,4]triazepin-3-yl)-acetic acid ethyl ester;

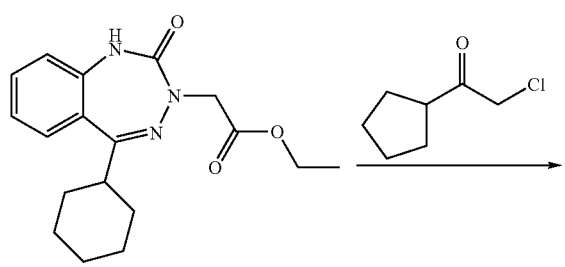

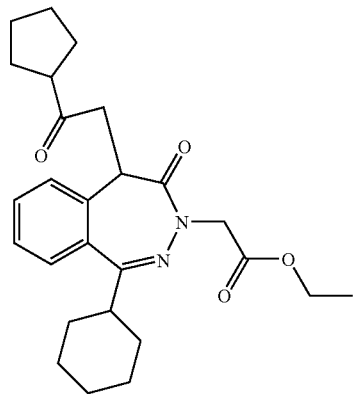

reacting the (5-cyclohexyl-2-oxo-1,2-dihydro-benzo[e][1,2,4]triazepin-3-yl)-acetic acid ethyl ester with 2-chloro-1-cyclopentyl-ethanone; in the presence of an organic or inorganic base; in an organic solvent; in the presence of a source of iodide; to yield [5-cyclohexyl-1-(2-cyclopentyl-2-oxo-ethyl)-2-oxo-1,2-dihydro-benzo[e][1,2,4]triazepin-3-yl]-acetic acid ethyl ester;

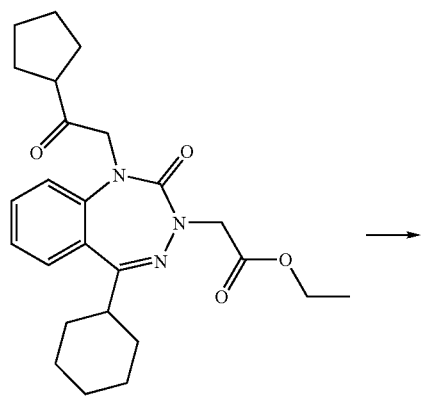

reacting the [5-cyclohexyl-1-(2-cyclopentyl-2-oxo-ethyl)-2-oxo-1,2-dihydro-benzo[e][1,2,4]triazepin-3-yl]-acetic acid ethyl ester is reacted with an aqueous base; to yield [5-cyclohexyl-1-(2-cyclopentyl -2-oxo-ethyl)-2-oxo-1,2-dihydro-benzo[e][1,2,4]triazepin-3-yl]-acetic acid;

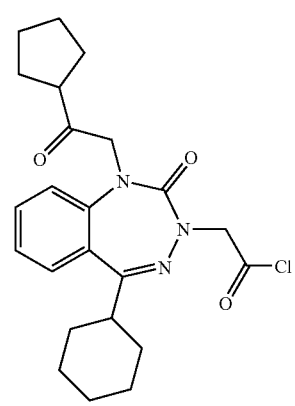

reacting the [5-cyclohexyl-1-(2-cyclopentyl-2-oxo-ethyl)-2-oxo-1,2-dihydro-benzo[e][1,2,4]triazepin-3-yl]-acetic acid with a chlorinating agent; in an organic solvent; to yield [5-cyclohexyl-1-(2-cyclopentyl-2-oxo-ethyl)-2-oxo-1,2-dihydro-benzo[e][1,2,4]triazepin-3-yl]-acetyl chloride;

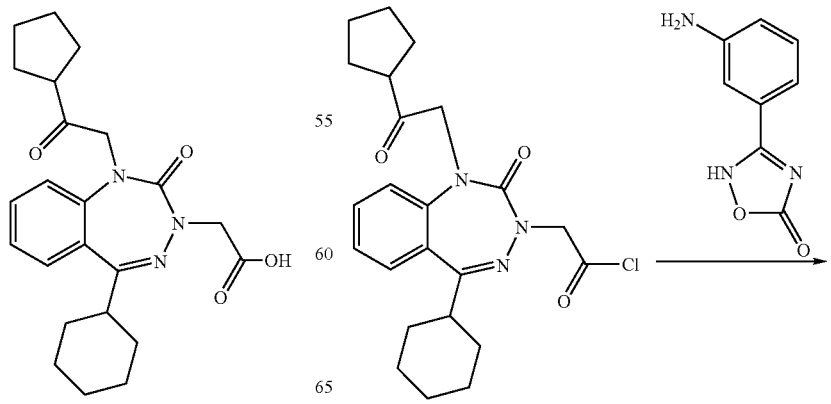

-continued

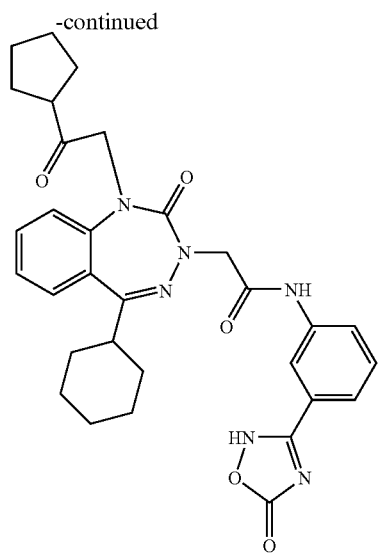

reacting the [5-cyclohexyl-1-(2-cyclopentyl-2-oxo-ethyl)-2-oxo-1,2-dihydro-benzo[e][1,2,4]triazepin-3-yl]-acetyl chloride with 3-(3-amino-phenyl)-2H-[1,2,4]oxadiazol-5-one; in the presence of an organic base; in an aprotic organic solvent; to yield the 2-[5-cyclohexyl-1-(2-cyclopentyl-2-oxo-ethyl)-2-oxo-1,2-dihydro-benzo[e][1,2,4]triazepin-3-yl]-N-[3-(5-oxo-2,5-dihydro-[1,2,4]oxadiazol-3-yl)-phenyl]-acetamide, the compound of formula (Is).

2. The process as in claim 1, wherein [5-cyclohexyl-1-(2-cyclopentyl-2-oxo-ethyl)-2-oxo-1,2-dihydro-benzo[e][1,2,4]triazepin-3-yl]-acetic acid is reacted with thionyl chloride in situ, in acetonitrile.

3. The process as in claim 2, wherein the 3-(3-amino-phenyl)-2H-[1,2,4]oxadiazol-5-one is reacted as its corresponding HCl salt; in the presence of about 2 equivalents of DIPEA; in acetonitrile.

\* \* \* \* \*